United States Patent
Chi

(10) Patent No.: US 11,520,031 B2
(45) Date of Patent: Dec. 6, 2022

(54) DOPPLER SIGNAL PROCESSING DEVICE AND METHOD THEREOF FOR INTERFERENCE SPECTRUM TRACKING AND SUPPRESSION

(71) Applicant: RichWave Technology Corp., Taipei (TW)

(72) Inventor: Hsiang-Feng Chi, Taipei (TW)

(73) Assignee: RichWave Technology Corp., Taipei (TW)

( * ) Notice: Subject to any disclaimer, the term of this patent is extended or adjusted under 35 U.S.C. 154(b) by 714 days.

(21) Appl. No.: 16/418,967

(22) Filed: May 21, 2019

(65) Prior Publication Data

US 2020/0003864 A1 Jan. 2, 2020

(30) Foreign Application Priority Data

Jun. 28, 2018 (TW) .................. 107122253

(51) Int. Cl.
*A61B 5/11* (2006.01)
*A61B 5/113* (2006.01)
(Continued)

(52) U.S. Cl.
CPC ............ *G01S 13/56* (2013.01); *A61B 5/1102* (2013.01); *A61B 5/113* (2013.01); *A61B 5/1126* (2013.01); *G01S 7/023* (2013.01); *G01S 7/415* (2013.01)

(58) Field of Classification Search
CPC .......... G01S 13/56; G01S 7/023; G01S 7/415; G01S 7/36; A61B 5/1102; A61B 5/1126; A61B 5/113
See application file for complete search history.

(56) References Cited

U.S. PATENT DOCUMENTS 5,309,161 A 5/1994 Urkowitz
6,091,361 A 7/2000 Davis
(Continued)

FOREIGN PATENT DOCUMENTS

CN 104586434 B 1/2017
CN 107144825 A 9/2017
(Continued)

OTHER PUBLICATIONS

Search report dated Dec. 4, 2019 for the EP Application No. 19182767.4, filing date Jun. 27, 2019, pp. 1-8.
(Continued)

*Primary Examiner* — Donald H B Braswell
(74) *Attorney, Agent, or Firm* — Winston Hsu

(57) ABSTRACT

Doppler signal processing device for detecting an object according to a received wireless signal. The Doppler signal processing device includes a frequency analysis unit for generating a frequency domain signal vector according to at least one digital signal, an interference suppression unit for performing a suppression operation according to the frequency domain signal vector and a frequency domain interference estimation signal vector to generate an interference suppressed frequency domain signal vector, an interference estimation unit for generating the frequency domain interference estimation signal vector according to the frequency domain signal vector, a detection unit for generating a result signal according to the interference suppressed frequency domain signal vector, an error detection unit for optionally providing an error detection control signal to the interference estimation unit to adjust a rate of updating the frequency domain interference estimation signal vector.

20 Claims, 9 Drawing Sheets

(51) Int. Cl.
    *G01S 7/02*         (2006.01)
    *G01S 7/41*         (2006.01)
    *G01S 13/56*      (2006.01)

(56) References Cited

U.S. PATENT DOCUMENTS

| | | | |
|---|---|---|---|
| 8,947,672 B2 | 2/2015 | Schmoll | |
| 2016/0195606 A1* | 7/2016 | Sugino | G01S 7/354 |
| | | | 342/195 |
| 2018/0106897 A1* | 4/2018 | Shouldice | G01S 13/56 |
| 2018/0263502 A1* | 9/2018 | Lin | A61B 5/05 |
| 2019/0015277 A1* | 1/2019 | Sauser | A61G 7/05769 |

FOREIGN PATENT DOCUMENTS

| | | |
|---|---|---|
| CN | 111077514 A | 4/2020 |
| EP | 2 857 860 A1 | 4/2015 |
| EP | 2 940 486 A1 | 11/2015 |
| EP | 3 588 126 A1 | 1/2020 |
| TW | 569008 | 1/2004 |
| TW | I315617 | 10/2009 |
| TW | I669522 B | 8/2019 |
| TW | 202028776 A | 8/2020 |

OTHER PUBLICATIONS

Office action dated Aug. 5, 2022 for the Taiwan application No. 110133880, filing date Sep. 11, 2021, pp. 1-6, Aug. 5, 2022.

* cited by examiner

DOPPLER SIGNAL PROCESSING DEVICE AND METHOD THEREOF FOR INTERFERENCE SPECTRUM TRACKING AND SUPPRESSION

CROSS REFERENCE TO RELATED APPLICATION

This application claims priority of Taiwan application no. 107122253, which was filed on Jun. 28, 2018, and is included herein by reference.

TECHNICAL FIELD

The present invention is related to a Doppler signal processing device, in particular, a Doppler signal processing device for a Doppler radar capable of interference spectrum tracking and suppression.

BACKGROUND

When using radar devices to detect objects, there is often the problem of background interference. For example, if a radar device is used to detect vital signs or human body, the background interference is often large, resulting in incorrect detection. In order to reduce the impact of background interference, signal energy threshold device or frequency energy detection method can be used to determine the detection results. However, these methods do not provide high accuracy detection results.

SUMMARY

The embodiment provides a Doppler signal processing device for detecting an object according to a received wireless signal. The Doppler signal processing device comprises a frequency analysis unit configured to generate a frequency domain signal vector according to at least one digital signal, an interference suppression unit configured to perform a suppression operation according to the frequency domain signal vector and a frequency domain interference estimation signal vector to generate an interference suppressed frequency domain signal vector, an interference estimation unit configured to generate the frequency domain interference estimation signal vector according to the frequency domain signal vector, a detection unit configured to generate a result signal according to the interference suppressed frequency domain signal vector, an error detection unit configured to optionally provide an error detection control signal to the interference estimation unit to adjust a rate of updating the frequency domain interference estimation signal vector.

Another embodiment provides a Doppler signal processing device for detecting an object according to a received wireless signal. The Doppler signal processing device comprises a frequency analysis unit configured to generate a frequency domain signal vector according to at least one digital signal, an interference subtracting unit configured to perform spectral subtraction according to the frequency domain signal vector and a frequency domain interference estimation signal vector to generate an amplitude value, a frequency domain detection threshold unit configured to generate a frequency domain detection threshold vector according to the frequency domain interference estimation signal vector and a first adjustment parameter, a detection unit configured to generate a result signal according to the frequency domain signal vector and the frequency domain detection threshold vector, an interference estimation unit configured to generate the frequency domain interference estimation signal vector according to the frequency domain signal vector, and an error detection unit configured to optionally provide an error detection control signal to the interference estimation unit according to the amplitude value to adjust a rate of updating the frequency domain interference estimation signal vector.

Another embodiment provides a method of signal processing. The method of signal processing comprises: generating a frequency domain signal vector according to the at least one digital signal, wherein the at least one digital signal comprises movement information of the object and an interference signal generated by an interference in the background, and the frequency domain signal vector comprising a frequency domain of a time period and a corresponding energy value; generating a frequency domain interference estimation signal vector according to the frequency domain signal vector, wherein the frequency domain interference estimation signal vector corresponds to an energy distribution in the frequency domain; providing optionally an error detection control signal to the interference estimation unit to adjust a rate of updating the frequency domain interference estimation signal vector, wherein the error detection control signal is provided according to whether the frequency domain interference estimation signal vector include Doppler energy of the object movement; and generating a result signal according to the frequency domain signal vector and the frequency domain detection threshold vector wherein the result signal is related to movement information of the object.

DETAILED DESCRIPTION

Figure 1:
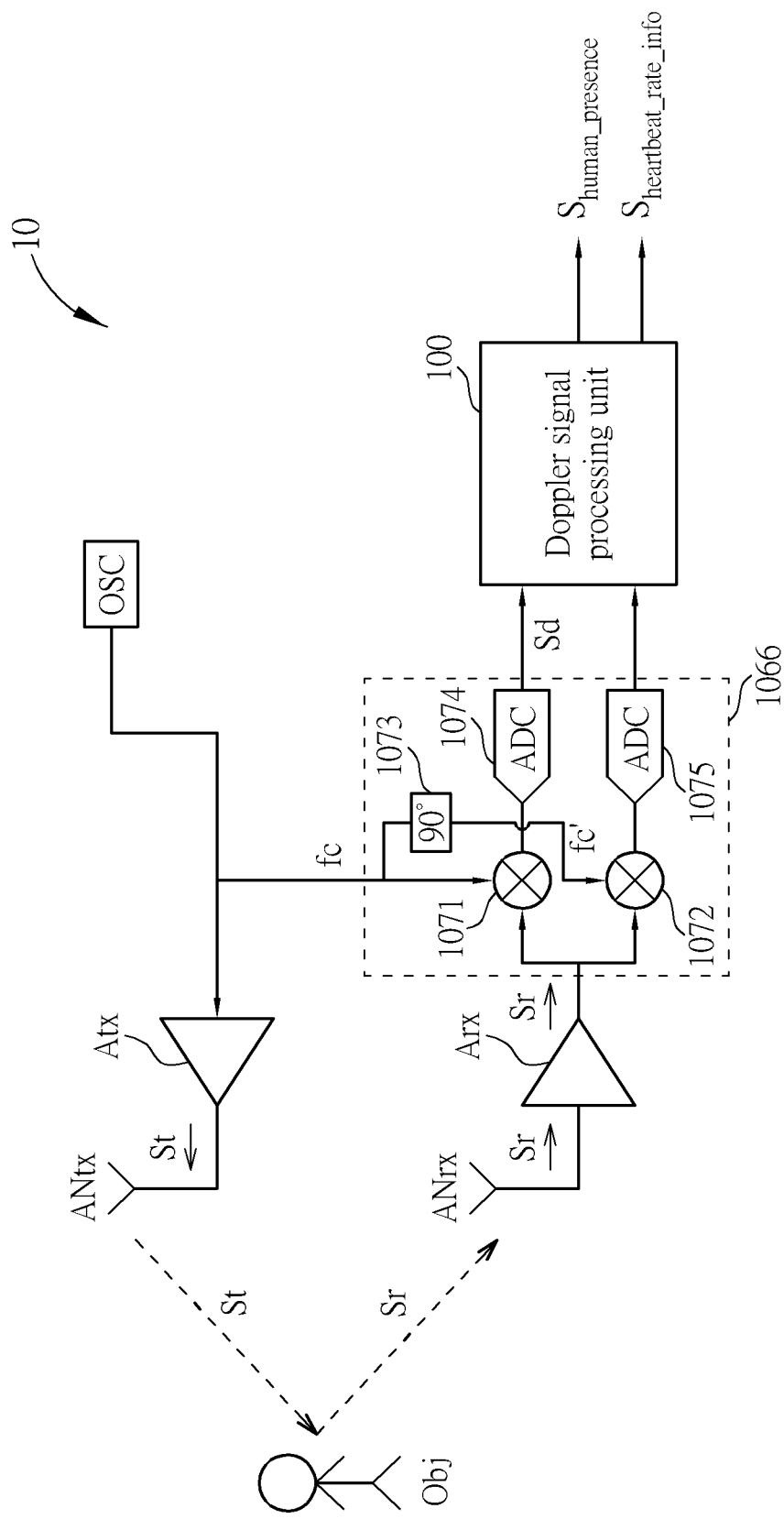
FIG. 1 is a diagram of a signal detecting device of an embodiment.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

FIG. 1 is a diagram of a signal detecting device 10 of an embodiment. The signal detecting device 10 can include antennas ANtx and ANrx, amplifying devices Atx and Arx, a receiving unit 1066, an oscillator OSC, and a Doppler signal processing device 100. The signal detecting device 10 can be used to perform Doppler radar motion detection. The oscillator OSC can provide a carrier signal fc, and the carrier signal fc can have a fixed frequency. The amplifying device Atx, such as a power amplifier Atx, can output a wireless transmission signal, such as a RF (radio frequency) transmission signal St, which is transmitted by the antenna ANtx. The RF transmission signal St can be generated according to the carrier signal fc. According to the embodiment, a generator for RF transmission signal St can be disposed optionally between the oscillator OSC and the amplifying device Atx according to the carrier signal fc. If an object Obj (for example, a human body) is present in the aperture of antenna ANTx, the object Obj reflects the RF transmission signal St, thereby scattering a wireless receiving signal, such as a RF receiving signal Sr. The antenna ANrx can receive the RF receiving signal Sr, which can be amplified by the amplifying device Arx, such as a low-noise amplifier Arx, and inputted to the receiving unit 1066. The receiving unit 1066 can generate at least one digital signal Sd according to the carrier signal fc and the RF receiving signal Sr. For example, the receiving unit 1066 can include mixers 1071 and 1072, phase shift unit 1073, and analog-to-digital converters (ADC) 1074 and 1075. The mixer 1071 can mix the carrier signal fc and the RF receiving signal Sr, and convert the result into a digital signal by the analog-to-digital converter 1074. The phase shift unit 1073 can shift the phase of the carrier signal fc by a specific angle (e.g., 90 degrees) to generate an adjusted carrier signal fc'. The mixer 1072 can mix the adjusted carrier signal fc' and the RF receiving signal Sr, and convert the result into a digital signal by the analog-to-digital converter 1075. The at least one digital signal Sd may include signals outputted by the analog-to-digital converters 1074 and 1075. The architecture of the receiving unit 1066 of FIG. 1 is only an example, and not to limit the circuit structure.

Figure 2:
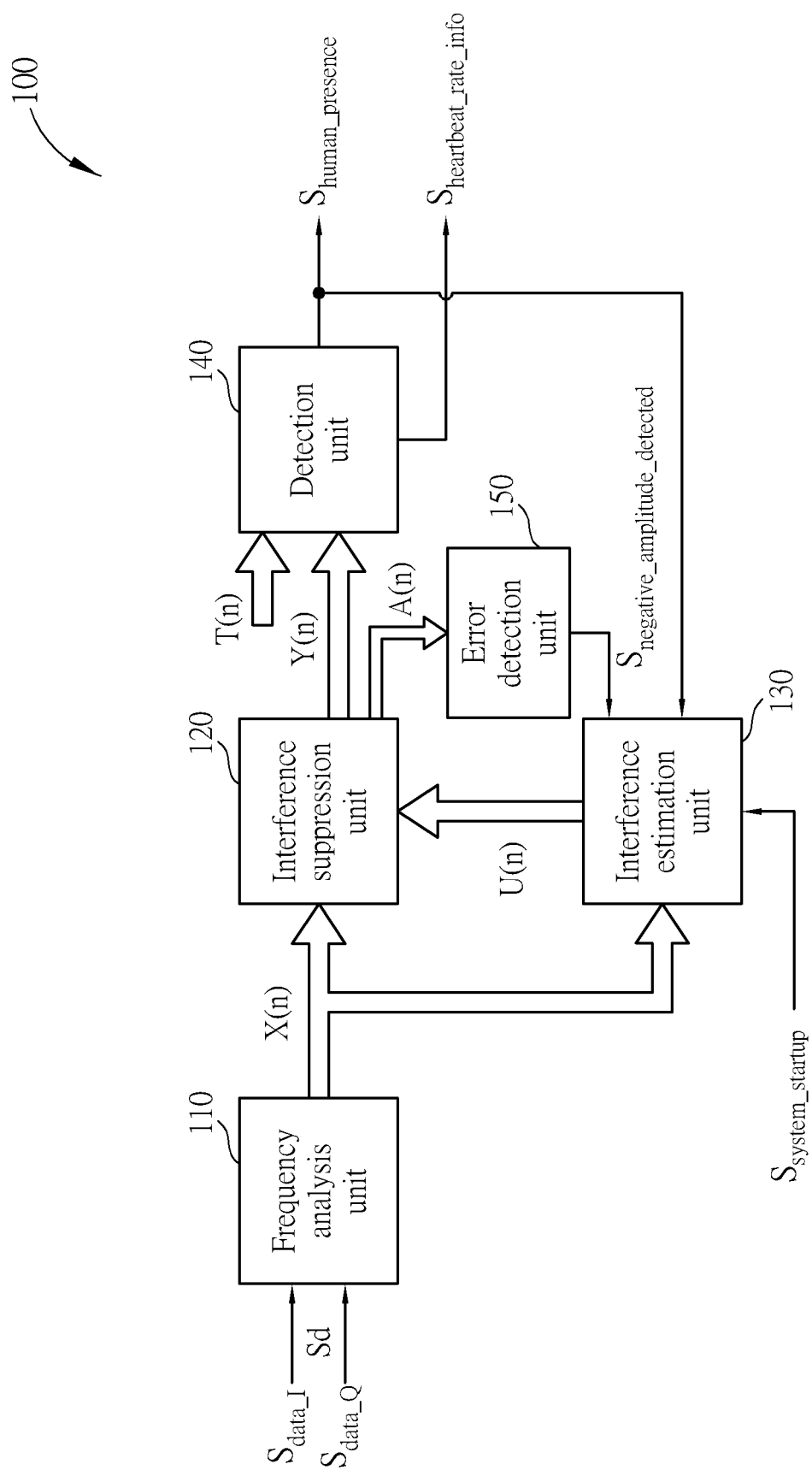
FIG. 2 is a diagram of the Doppler signal processing device of FIG. 1.

FIG. 2 is a diagram of the Doppler signal processing device 100 of FIG. 1. The Doppler signal processing device 100 may include a frequency analysis unit 110, an interference suppression unit 120, an interference estimation unit 130, a detection unit 140, and an error detection unit 150. The frequency analysis unit 110 may be configured to generate a frequency domain signal vector X(n) according to the at least one digital signal Sd. The frequency analysis unit 110 can apply fast Fourier transform (FFT) to implement short-time Fourier transform (STFT), which may also be a multi-band filter bank that performs a multi-band filtering operation using the at least one digital signal Sd.

The digital signal Sd can correspond to the RF receiving signal Sr. The information carried by the digital signal Sd can include the spatial and movement information of the object Obj and an interference in the background. The frequency domain signal vector X(n) may include a frequency domain of a time period and a corresponding energy value, such as multi-frequency frequency domain or multi-band frequency domain of a time period, or a multi-band signal vector.

According to the embodiment, the digital signal Sd can include at least one of digital signals $S_{data\_I}$ and $S_{data\_Q}$ as shown in FIG. 2, wherein the digital signal $S_{data\_I}$ can be an in-phase signal, and the digital signal $S_{data\_Q}$ can be a quadrature signal, so the digital signals $S_{data\_I}$ and $S_{data\_Q}$ can be applied to the IQ modulation.

The interference suppression unit 120 may be configured to perform a suppression operation to generate an interference suppressed frequency domain signal vector Y(n) according to the frequency domain signal vector X(n) and the frequency domain interference estimation signal vector U(n). In the interference suppressed frequency domain signal vector Y(n), energy distribution of the above-mentioned background interference in the frequency domain can be suppressed. In other words, in the interference suppressed frequency domain signal vector Y(n), the interference of a specific frequency band can be reduced. The vector in the frequency domain signal vector X(n), the interference suppressed frequency domain signal vector Y(n) and the frequency domain interference estimation signal vector U(n) are, for example, sets of data.

The interference estimation unit 130 may be configured to track the interference energy spectrum caused by interference in the background according to the frequency domain signal vector X(n) and generate/update a frequency domain interference estimation signal vector U(n). The frequency domain interference estimation signal vector U(n) may correspond to an energy distribution interference in the frequency domain. The frequency domain interference estimation signal vector U(n) may include a frequency domain interference energy baseline component of a steady state, and the interference estimation unit 130 may be a frequency domain interference energy baseline estimation unit.

The detection unit 140 may be configured to generate a result signal $S_{human\_presence}$ according to the interference suppressed frequency domain signal vector Y(n) and a frequency domain detection threshold vector T(n). The frequency domain detection threshold vector T(n) may be substantially fixed. The result signal $S_{human\_presence}$ can be related to the movement information of the object Obj. For example, the spatial and movement information may include the displacement of the object Obj, and the moving speed of the object Obj, etc. The result signal $S_{human\_presence}$ can be used to determine whether the object Obj, such as a human body, has been detected. The detection unit 140 can optionally provide heartbeat information signal $S_{heartbeat\_rate\_info}$ to provide the heartbeat information of survivors according to the reflected Doppler signal. The detection unit 140 may also be configured to generate the result signal $S_{human\_presence}$ according to the interference suppressed frequency domain signal vector Y(n).

The error detection unit 150 may be configured to optionally provide an error detection control signal $S_{negative\_amplitude\_detected}$ to the interference estimation unit 130 to adjust the rate of updating the frequency domain interference estimation signal vector U(n), wherein the error detection control signal $S_{negative\_amplitude\_detected}$ refers to whether the frequency domain interference estimation signal vector U(n) incorrectly includes the moving Doppler energy of the object Obj in the frequency domain. In other words, the frequency domain interference estimation signal vector U(n) should only include the interference energy distribution in the frequency domain and independent of the movement of the object Obj. However, if the frequency domain interference estimation signal vector U(n) unexpectedly include the movement of the object Obj due to the Doppler signal processing device 100 switching from off state to on, the frequency domain interference estimation signal vector U(n) U(n) would erroneously include the moving Doppler energy. When this happens, the error detection unit 150 can provide the error detection control signal $S_{negative\_amplitude\_detected}$. The frequency domain interference estimation signal vector U(n) is related to whether the moving Doppler energy of the object Obj is included. The rate of updating interference estimate signal vector U(n) would be adjusted to a faster rate, a slower rate, or stopping the update.

According to the embodiment, the interference suppression unit 120 may further provide an amplitude value A(n) to the error detection unit 150, so that the error detection unit 150 asserts or de-asserts the error detection control signal $S_{negative\_amplitude\_detected}$. For example, when the amplitude value A(n) reaches a certain negative value, the value of the error detection control signal $S_{negative\_amplitude\_detected}$ can be set to 1, and vice versa. If it is used to detect a human body, such as a survivor, the Doppler signal processing device 100 can be a human presence sensing system.

According to the frequency domain signal vector X(n) and the frequency domain interference estimation signal vector U(n) shown in FIG. 2, the following equations can be provided.

$$A(n) = |X(n)| - \alpha \cdot U(n) \quad (1)$$

$$B(n) = (|X(n)|/(1 + \beta \cdot U(n))) \exp(j \angle X(n)) \quad (2)$$

$$Y(n) = A(n) \exp(j \angle X(n)) \quad (3)$$

$$Y(n) = B(n) \exp(j \angle X(n)) \quad (4)$$

Equations (1) and (3) can be applied in one embodiment and equations (2) and (4) can be applied to another embodiment.

According to the embodiment, spectral subtraction may be performed, and as shown in equation (1) to obtain the amplitude value A(n) and the interference suppressed frequency domain signal vector Y(n) can be obtained through equation (3). As shown in equation (1), an absolute value |X(n)| of the frequency domain signal vector X(n) can be obtained, and the product $\alpha \cdot U(n)$ of the frequency domain interference estimation signal vector U(n) and the adjustment parameter $\alpha$ can also be obtained. Finally one can obtain the difference between the absolute value |X(n)| and the product $\alpha \cdot U(n)$ and obtain the amplitude value A(n). Then, as in equation (3), the angle value of the frequency domain signal vector X(n) can be substituted into Euler formula to get $\exp(j \cdot \angle X(n))$. The amplitude value A(n) is multiplied by $\exp(j \cdot \angle X(n))$ to get a interference suppressed frequency domain signal vector Y(n).

In another embodiment, spectrum weighting can be performed, as shown by equation (2), to obtain a weight value B(n). The interference suppressed frequency domain signal vector Y(n) can be obtained by equation (4). The absolute value |X(n)| of the frequency domain signal vector X(n) can be obtained in equation (2), and the product $\beta \cdot U(n)$ of the frequency domain interference estimation signal vector U(n) and the adjustment parameter $\beta$ can also be obtained. Further, by adding a constant (for example, 1) to the product $\beta \cdot U(n)$, finding an adjustment parameter $(1 + \beta \cdot U(n))$, and dividing the absolute value |X(n)| by the adjustment parameter $(1 + \beta \cdot U(n))$, one obtain $|X(n)|/(1 + \beta \cdot U(n))$. Substituting the angle value of the frequency domain signal vector X(n) into the Euler's formula yields $\exp(j \cdot \angle X(n))$. Multiplying $|X(n)|/(1 + \beta \cdot U(n))$ by $\exp(j \cdot \angle X(n))$ gives the weight value B(n). Further in equation (4), by multiplying the weight value B(n) by $\exp(j \cdot \angle X(n))$, the interference suppressed frequency domain signal vector Y(n) can be obtained. In the equations, $\alpha$ and $\beta$ can be suitable adjustment parameters, j represents an imaginary unit, and $\angle$ can represent an angle value.

The frequency domain signal vector X(n), the interference suppressed frequency domain signal vector Y(n), and the frequency domain interference estimation signal vector U(n) may be signal vectors in frequency domain, wherein the variable n may be a time index corresponding to discrete intervals on time axis.

The above-mentioned interference can be caused, for example, by a constant rotating fan or an electric appliance operating at a constant voltage frequency, so the interference energy distribution in frequency domain is substantially fixed. The result signal $S_{human\_presence}$ can be used to determine whether the object Obj is detected. If the object Obj is a human body, the result signal $S_{human\_presence}$ can be used to determine whether the human body exists. For example, such detection can be performed in situation such as a fire or an earthquake. According to the embodiment, the interference suppression unit 120 may generate the amplitude value A(n) according to the frequency domain signal vector X(n) and the frequency domain interference estimation signal vector U(n). When the amplitude value A(n) exceeds a certain negative value, the error detection unit 150 can provide the error detection control signal $S_{negative\_amplitude\_detected}$ to the interference estimation unit 130 to adjust the rate of updating the frequency domain interference estimation signal vector U(n). The amplitude value A(n) may be expressed as $A(n) = |X(n)| - \alpha \cdot U(n)$. Therefore, the error detection unit 150 can be a negative amplitude detection unit.

The frequency analysis unit 110 may perform function of a filter bank or perform a short-time Fourier transform (STFT) to generate a frequency domain signal vector X(n).

The interference estimation unit 130 can generate/update the frequency domain interference estimation signal vector U(n) according to the frequency domain signal vector X(n) and according to the result signal $S_{human\_presence}$.

The detection unit 140 can perform bin-by-bin detection and/or band-by-band detection, which corresponds to the detection threshold value of each bin and each band and is proportional to the absolute value |U(n)| of the frequency domain interference estimation signal vector U(n).

Figure 3:
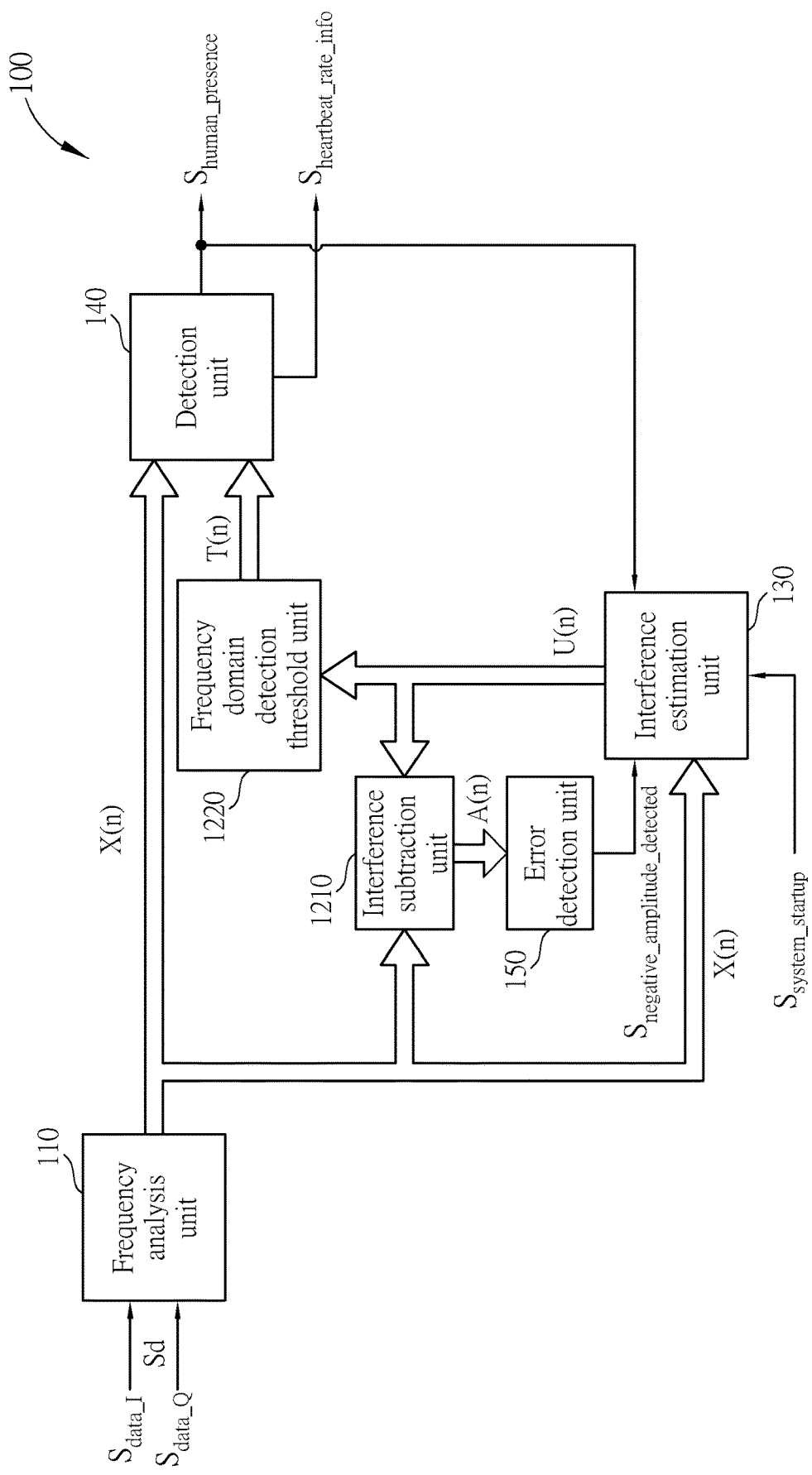
FIG. 3 is a diagram of the Doppler signal processing device in another embodiment.

FIG. 3 is a diagram of the Doppler signal processing device 100 in another embodiment. As shown in FIG. 3, the Doppler signal processing device 100 can include a frequency analysis unit 110, an interference estimation unit 130, a detection unit 140, an interference subtraction unit 1210, an error detection unit 150, and a frequency domain detection threshold unit 1220. The interference subtraction unit 1210 can perform spectral subtraction to generate an amplitude value A(n).

The frequency domain detection threshold unit 1220 can provide a detection threshold for the detection unit 140 in different frequency bins or frequency bands. The detection unit 140 will perform bin-by-bin detection or band-by-band detection according to the frequency domain signal vector X(n) if the energy of the frequency domain signal vector X(n) in the frequency bin or frequency band exceeds the bin-by-bin detection threshold or band-by-band detection threshold. This frequency can be determined as having the Doppler energy of the movement of the object, and then the result signal $S_{human\_presence}$ can be set to 1. The detection threshold constitutes the frequency domain detection threshold vector T(n).

The frequency domain detection threshold vector T(n) can be determined by the following equation:

$$T(n) = \gamma \cdot U(n) \quad (5)$$

where $\gamma$ can be an adjustment parameter.

For example, the amplitude of a bin of frequency domain detection threshold vector T(n) is proportional to the amplitude of the corresponding bin of frequency domain interference estimation signal vector U(n). The higher the energy of interference at a certain frequency bin is, the larger the detection threshold at that frequency should be.

Figure 4:
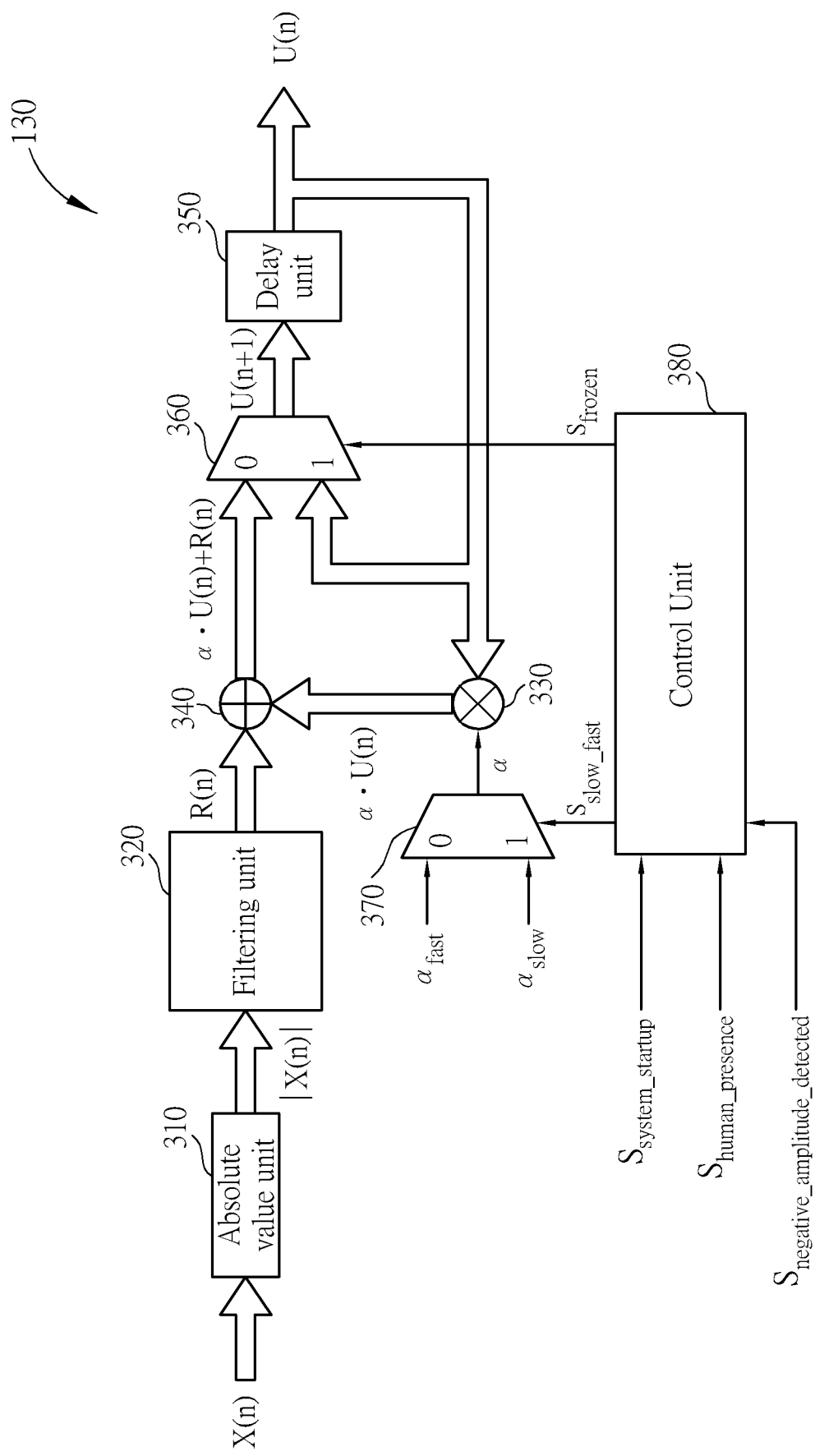
FIG. 4 is a diagram of the interference estimation unit in FIG. 2.

FIG. 4 is a diagram of the interference estimation unit 130 in FIG. 2 or FIG. 3. The interference estimation unit 130 may include an absolute value unit 310, a filtering unit 320, a multiplier 330, and an adder 340.

The absolute value unit 310 can generate an absolute value |X(n)| of the frequency domain signal vector X(n). The filtering unit 320 can generate a corresponding filtered signal vector R(n) according to the absolute value |X(n)|. The filtering unit 320 can be a median filter unit, wherein the $k_{th}$ element of the frequency domain signal vector X(n) is the $k_{th}$ bin or band and may be expressed as $X_k(n)$. The $k_{th}$ bin or band of the filtered signal vector R(n) may be expressed as $R_k(n)$, where n is a time index. When the size of the median filter window of the filtering unit 320 is M, then $R_k(n)$ can be expressed as the median value of $R_k(n)\{X_k(n), X_k(n-1), \ldots, X_k(n-M+1)\}$.

The multiplier 330 can generate a product $\alpha \cdot U(n)$ of a frequency domain interference estimation signal vector U(n) and the adjustment parameter $\alpha$. The adder 340 can generate a sum of the product $\alpha \cdot U(n)$ and the filtered signal vector R(n), that is, $\alpha \cdot U(n) + R(n)$. The sum value $\alpha \cdot U(n) + R(n)$ can be used to update the frequency domain interference estimation signal vector U(n).

The interference estimation unit 130 can optionally include a delay unit 350. The delay unit 350 can delay the sum $\alpha \cdot U(n) + R(n)$ by a predetermined delay time and update the frequency domain interference estimation signal vector U(n).

The interference estimation unit 130 can optionally include a multiplexer 360. The multiplexer 360 can be disposed between the adder 340 and the delay unit 350 to determine the whether to output the updated the frequency domain interference estimation signal vector U(n) or the original frequency domain interference estimation signal vector U(n) according to a selection signal $S_{frozen}$.

The interference estimation unit 130 can optionally include a multiplexer 370. The multiplexer 370 can be disposed at the input terminal of the mixer 330 for selecting to output the first parameter $\alpha_{fast}$ or output the second parameter $\alpha_{slow}$ to the mixer 330 according to the selection signal $S_{slow\_fast}$ to adjust the parameter a. The first parameter $\alpha_{fast}$ may be greater than the second parameter $\alpha_{slow}$, and the first parameter $\alpha_{fast}$ and the second parameter $\alpha_{slow}$ may both be greater than 0 and less than 1.

For example, if the result signal $S_{human\_presence}$ in FIG. 2 is substantially unchanged, and the human body is detected continually, the selection signal $S_{frozen}$ can be 1 to stop updating the frequency domain interference estimation signal vector U(n). Setting the selection signal $S_{frozen}$ without updating the frequency domain interference estimation signal vector U(n) may be referred to as a frozen operation. Therefore, the selection signal $S_{frozen}$ can be referred to as a frozen signal.

The interference estimation unit 130 can also generate the frequency domain interference estimation signal vector U(n) according to the startup signal $S_{system\_startup}$. The startup signal $S_{system\_startup}$ may correspond to startup of the Doppler signal processing device 100. According to the embodiment, the interference estimation unit 130 may further include a control unit 380 for generating the selection signal $S_{frozen}$ according to a change in the result signal $S_{human\_presence}$, and generating a selection signal $S_{slow\_fast}$ according to the change of the amplitude value A(n). In other words, the control unit 380 can determine the values of selection signals $S_{frozen}$ and $S_{slow\_fast}$.

Regarding selecting the first parameter $\alpha_{fast}$ or the second parameter $\alpha_{slow}$ to update the adjustment parameter $\alpha$, it will be described in the following paragraphs.

When the amplitude value A(n) reaches a certain negative value, the error detection unit 150 may assert the error detection signal $S_{negative\_amplitude\_detected}$. For example, it may change the value of the error detection signal $S_{negative\_amplitude\_detected}$ from 0 to 1 so as to let the control unit 380 output the selection signal $S_{slow\_fast}$. Then, the multiplexer 370 would output the first parameter $\alpha_{fast}$. In the example of FIG. 4, the value of the selection signal $S_{slow\_fast}$ may be 0, and the adjustment parameter $\alpha$ is updated according to the first parameter $\alpha_{fast}$ to speed up the update.

When the amplitude value A(n) does not exceed a certain negative value, for example A(n) being positive, the error detection unit 150 may de-assert the error detection control signal $S_{negative\_amplitude\_detected}$. The value of $S_{negative\_amplitude\_detected}$ may be changed from 0 to 1, so the control unit 380 outputs the selection signal $S_{slow\_fast}$ and makes the multiplexer 370 output the second parameter $\alpha_{slow}$. In the example of FIG. 4, the value of the selection signal $S_{slow\_fast}$ may be 1, and the adjustment parameter $\alpha$ is updated according to the second parameter $\alpha_{slow}$ to reduce the update rate.

Figure 5:
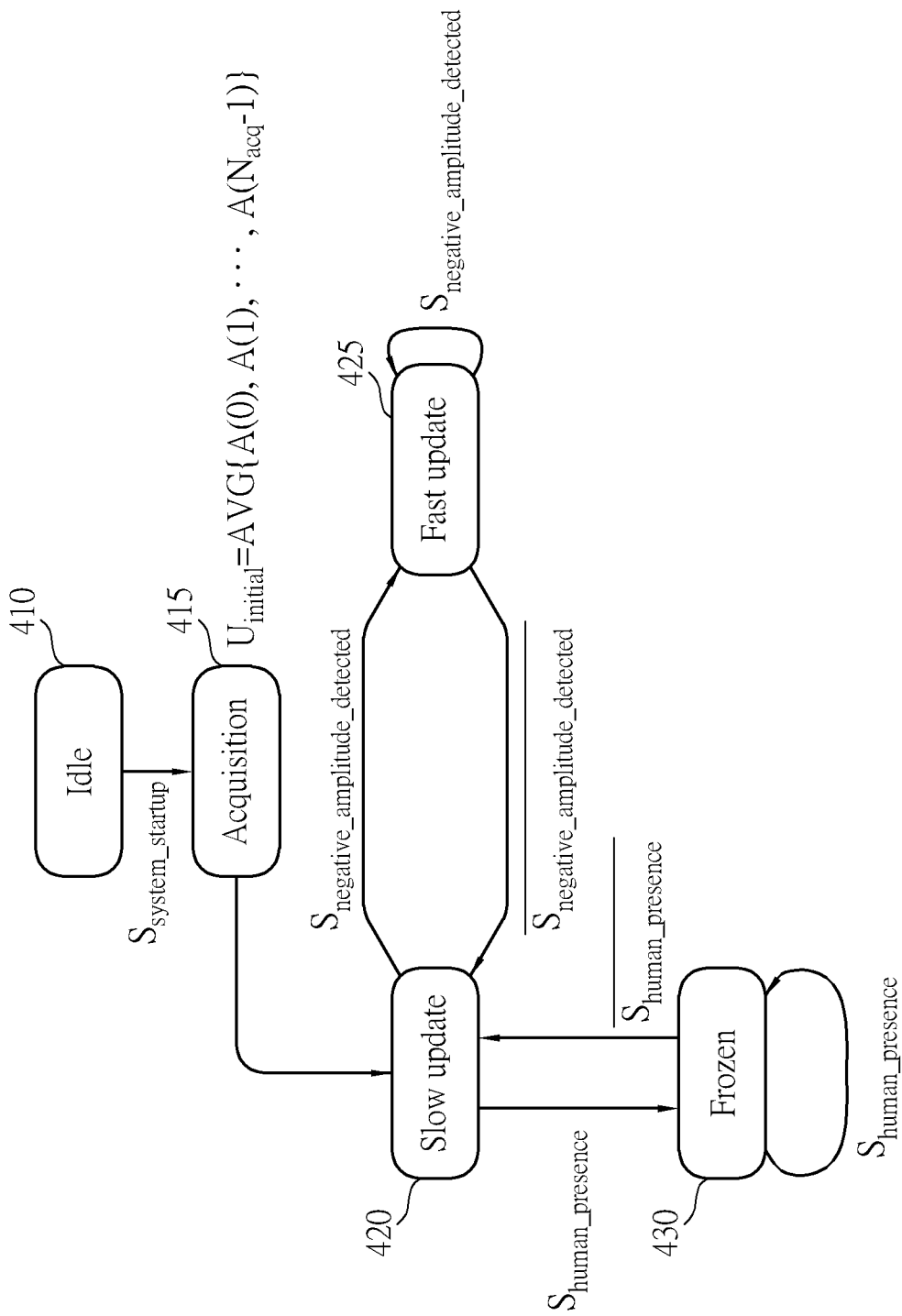
FIG. 5 is a diagram of a finite state machine of the control unit in FIG. 4.

FIG. 5 is a diagram of a finite state machine of the control unit 380 in FIG. 4. State 410 may be an idle state corresponding to the case where the Doppler signal processing device 100 is idle. When the Doppler signal processing device 100 is starting, the startup signal $S_{system\_startup}$ would be transmitted. As the information of the object Obj is received, the initial value $U_{initial}$ of the frequency domain interference estimation signal vector U(n) can be obtained and then entering state 415. State 415 is an information acquisition state. Wherein, $U_{initial}$ can be an average of a plurality of amplitude values, for example, $U_{initial}$=AVG{R(0), R(1), \ldots, R($N_{acq}$-1)}. AVG{ } can be an averaging function. R(n) can be the filtered signal vector at the $n_{th}$ point, $0 \leq n < N_{acq}$. Variable $N_{acq}$ can be a positive integer greater than 0 and can be set according to the specifications.

After state 415, the machine enters state 420. State 420 can be a slow update state. For example, in FIG. 2 or FIG. 3 and FIG. 4, in the state 420, the error detection control signal $S_{negative\_amplitude\_detected}$ may be at disable level. The selection signal $S_{slow\_fast}$ may control the multiplexer 370 to update the adjustment parameter $\alpha$ by the second parameter $\alpha_{slow}$ so that the frequency domain interference estimation signal vector U(n) can be updated slowly.

If A(n) reaches a certain negative value, the error detection control signal $S_{negative\_amplitude\_detected}$ can be pulled to enable level and entering state 425. State 425 can be a fast update state. In state 425, the selection signal $S_{slow\_fast}$ can control the multiplexer 370 to update the adjustment parameter a by the first parameter $\alpha_{fast}$ so that the frequency domain interference estimate signal vector U(n) can be updated quickly.

In state 420, the machine can enter state 425 when the error detection control signal $S_{negative\_amplitude\_detected}$ is pulled to enable level. In state 425, when the error detection control signal $S_{negative\_amplitude\_detected}$ is still at enable level, it can remain in state 425. When the error detection control signal $S_{negative\_amplitude\_detected}$ is pulled to disable level, the machine can enter state 420. It can be expressed as $\overline{S_{negative\_amplitude\_detected}}$.

In state 420, when the result signal $S_{human\_presence}$ is pulled to the enable level, it may correspond to the detection of the object Obj (e.g., detecting vital signs of a human body). At which point it enters state 430. State 430 can be a frozen state. In state 430, if the result signal $S_{human\_presence}$ remains at the enable level for a subsequent period of time, that is corresponding to the detected state of the object Obj, it may remain in state 430. If in state 430, the result signal $S_{human\_presence}$ is pulled to disable level, it enters state 420 which corresponds to not detecting the object Obj. The result signal $S_{human\_presence}$ is at disable level and can be expressed as the result signal $\overline{S_{human\_presence}}$.

Figure 6:
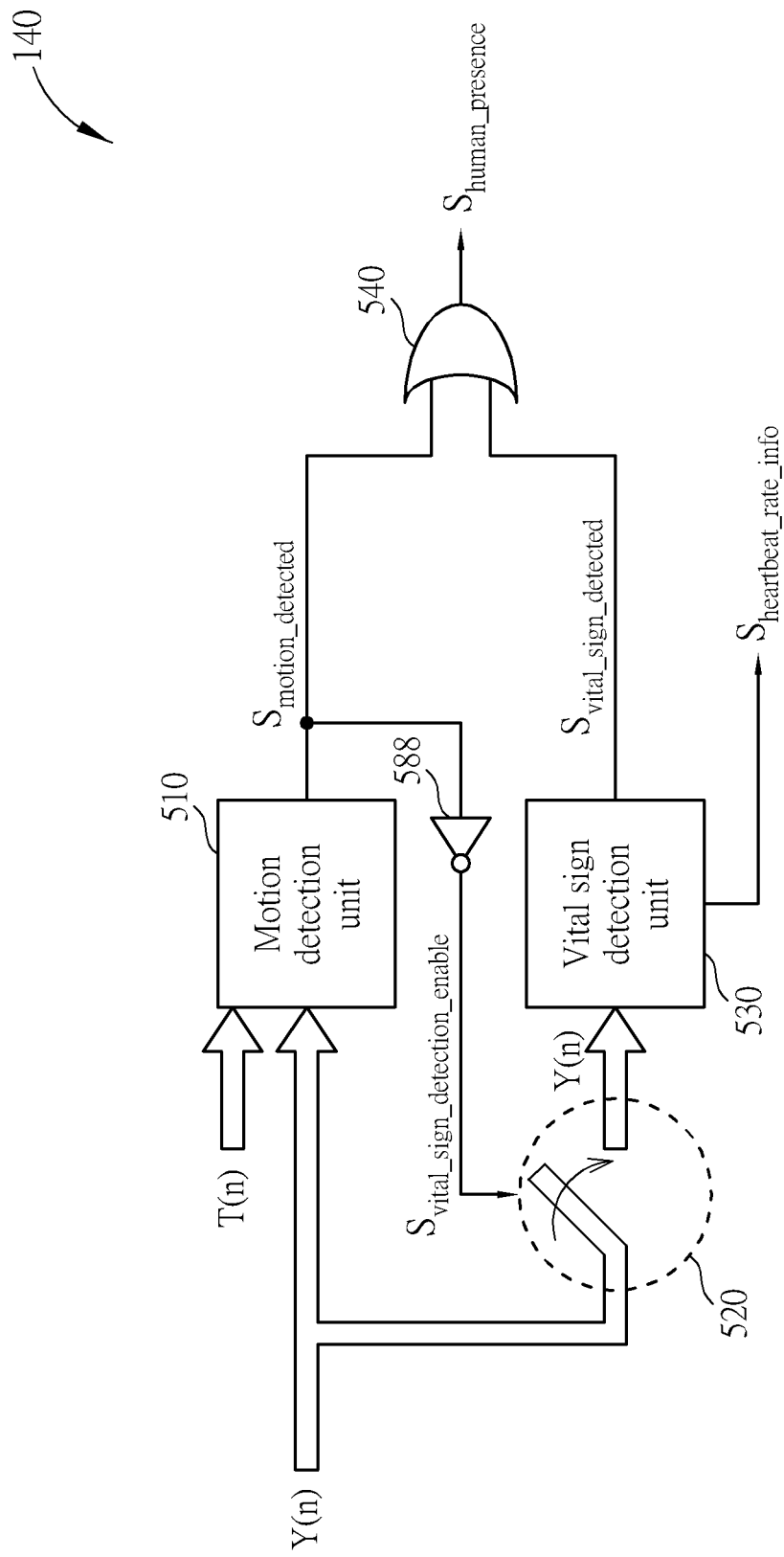
FIG. 6 is a diagram of the detection unit in FIG. 2.

FIG. 6 is a diagram of the detection unit 140 in FIG. 2. The detection unit 140 can include a motion detection unit 510, a switch unit 520, a vital sign detection unit 530, and an OR gate unit 540.

The motion detection unit 510 can generate a motion detection signal $S_{motion\_detected}$ according to the interference suppressed frequency domain signal vector Y(n), wherein the motion detection signal $S_{motion\_detected}$ corresponds to detecting the movement of the object Obj. The motion detection unit 510 can also generate a motion detection signal $S_{motion\_detected}$ according to the interference suppressed frequency domain signal vector Y(n) and the frequency domain detection threshold vector T(n).

The switch unit 520 can output the interference suppressed frequency domain signal vector Y(n) when the motion detection signal $S_{motion\_detected}$ corresponds to the case where the movement of the object Obj is not detected. In order to perform the operation, the detection unit 140 further includes an inverter 588 coupled between the output terminal of the motion detection unit 510 and the control terminal of the switch unit 520. The inverter 588 can invert the motion detection signal $S_{motion\_detected}$ to generate a vital sign detection enable signal $S_{vital\_sign\_detection\_enable}$, so the switch unit 520 is turned off when the movement of the object Obj is detected. The switch unit 520 is turned on when the movement of object Obj is not detected. FIG. 6 is merely an example for describing the principle of operation. The switch unit 520 may operate in different states, and the inverter 588 may not be required.

The vital sign detection unit 530 can receive the interference suppressed frequency domain signal vector Y(n) through the switch unit 520 and output the vital sign detection signal $S_{vital\_sign\_detected}$ when the motion detection signal $S_{motion\_detected}$ corresponds to not detecting the movement of the object Obj. The vital sign detection signal $S_{vital\_sign\_detected}$ can correspond to vital signs, such as heartbeat and breathing. The vital sign detection unit 530 can optionally provide the heartbeat information signal $S_{heartbeat\_rate\_info}$. That is, the vital signs are caused by tiny movements, such as heartbeat, breathing . . . etc., and the vital sign detection unit 530 can be a tiny motion detection unit, which can detect the tiny movement of the object Obj. For example, the tiny movement of the object Obj is much smaller than the movement (walking, waving . . . etc) of the object Obj being detected by the motion detection unit 510.

The OR gate unit 540 can output the result signal $S_{human\_presence}$ according to the motion detection signal $S_{motion\_detected}$ and the vital sign detection signal $S_{vital\_sign\_detected}$. When the movement of the object Obj or a vital sign is detected, the level of the signal $S_{human\_presence}$ may correspond to whether the object Obj is detected. In the situation of searching for the survivors, as long as at least one vital sign is detected, the presence of human body is determined to be detected.

The signal value mentioned above being 0 or 1, is merely an example for explaining the operation of the embodiment. According to another embodiment, the signal value when triggering the signal can also be 0, and the signal value when cancelling the signal can be 1, which is determined according to the circuit. The functional units and circuits described in FIGS. 1 to 6 are not limited to those shown in the drawings.

Figure 7:
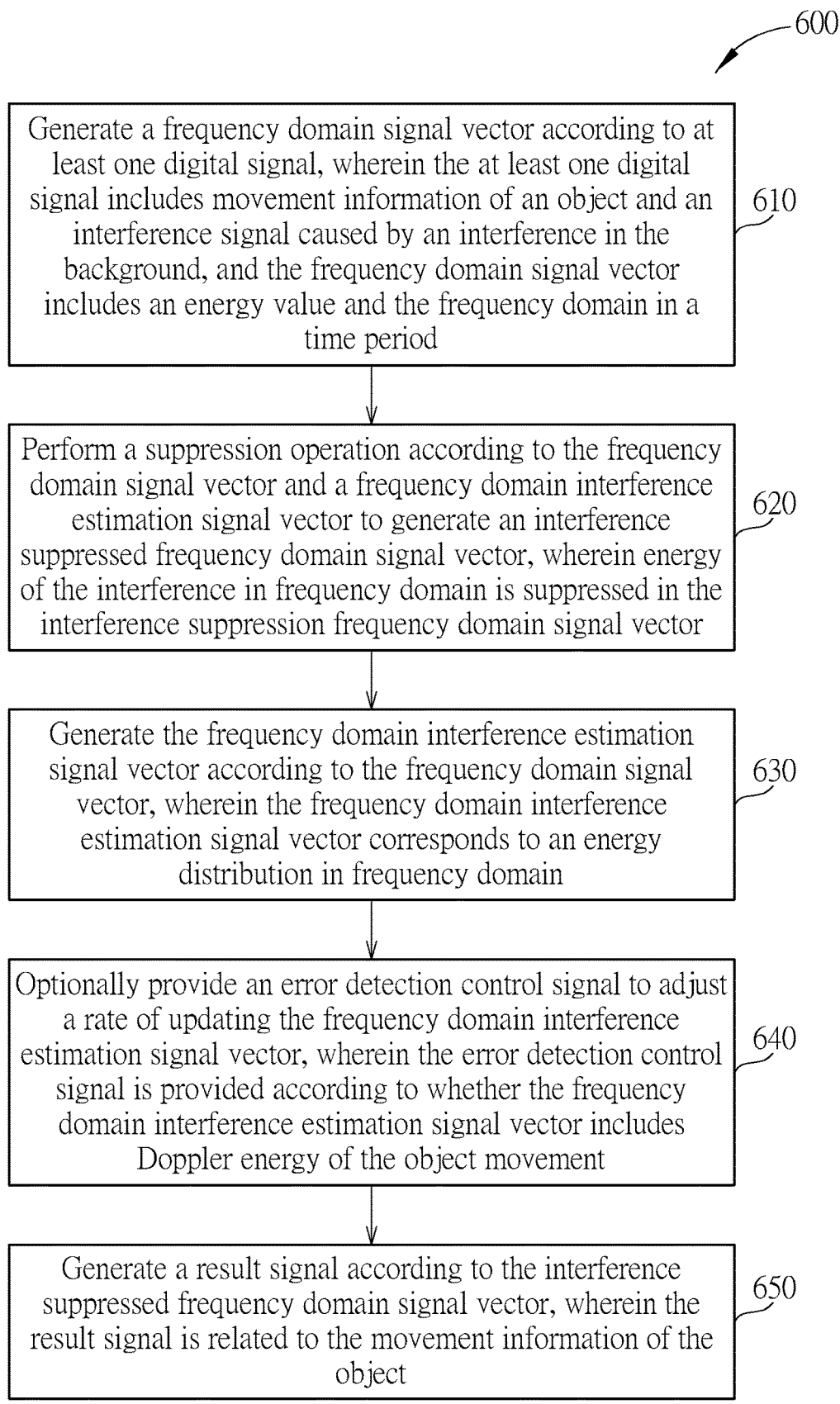
FIG. 7 is a flow chart of a signal processing method.

FIG. 7 is a flow chart of a signal processing method 600. As shown in FIGS. 2 and 7, the signal processing method 600 can include the following steps:

Step 610: Generate a frequency domain signal vector according to at least one digital signal, wherein the at least one digital signal includes movement information of an object and an interference signal caused by an interference in the background, and the frequency domain signal vector includes an energy value and the frequency domain in a time period;

Step 620: Perform a suppression operation according to the frequency domain signal vector and a frequency domain interference estimation signal vector to generate an interference suppressed frequency domain signal vector, wherein energy of the interference in frequency domain is suppressed in the interference suppressed frequency domain signal vector;

Step 630: Generate the frequency domain interference estimation signal vector according to the frequency domain signal vector, wherein the frequency domain interference estimation signal vector corresponds to an energy distribution in frequency domain;

Step 640: Optionally provide an error detection control signal to adjust a rate of updating the frequency domain interference estimation signal vector, wherein the error detection control signal is provided according to whether the frequency domain interference estimation signal vector includes Doppler energy of the object movement; and Step 650: Generate a result signal according to the interference suppressed frequency domain signal vector, wherein the result signal is related to the movement information of the object.

The detail operation of each step can be found in the above descriptions of FIG. 2 and FIG. 4 to FIG. 6 and would not be repeated here.

Figure 8:
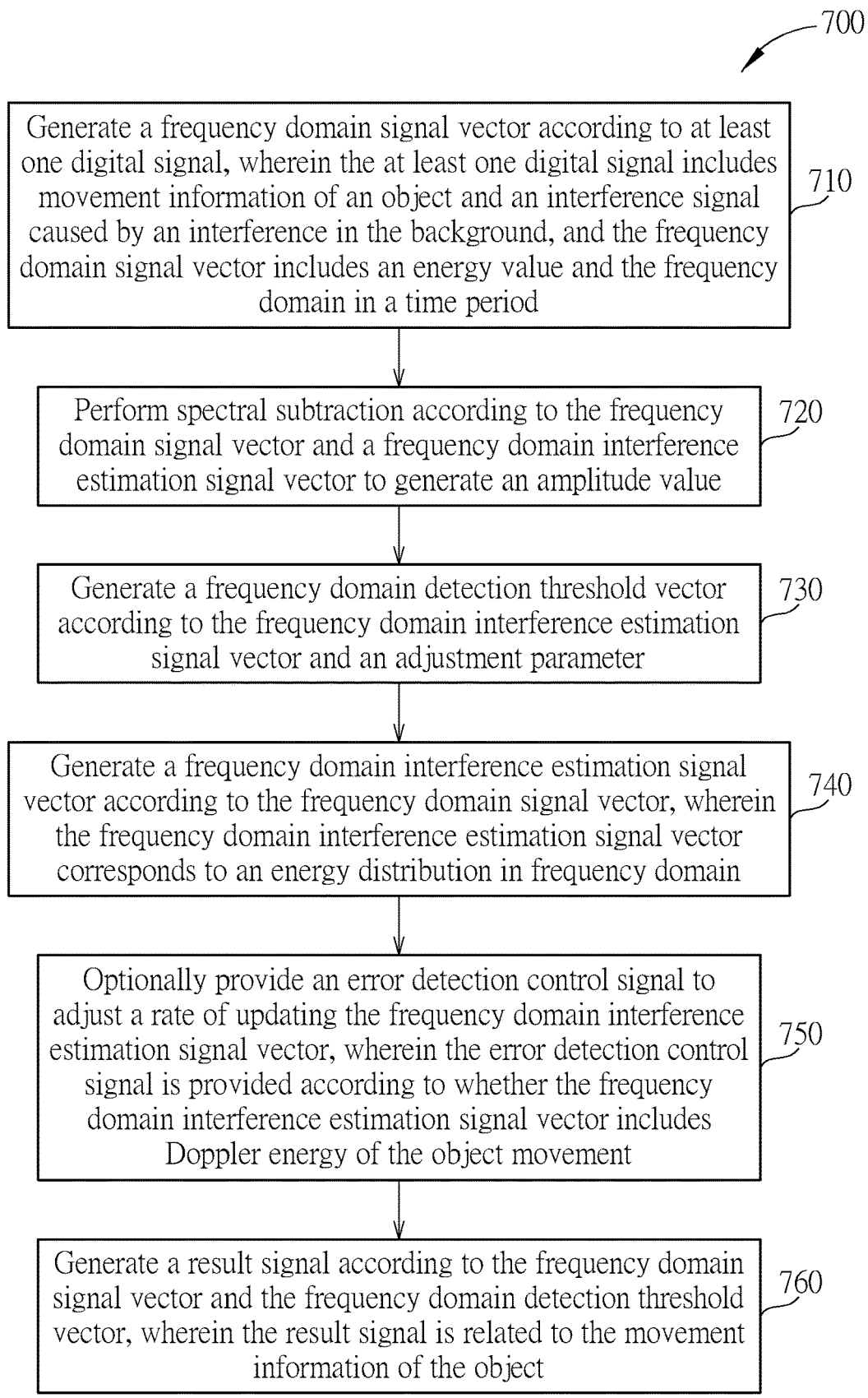
FIG. 8 is a flow chart of a signal processing method.

FIG. 8 is a flow chart of a signal processing method 700. As shown in FIGS. 3 and 8, the signal processing method 700 can include the following steps:

Step 710: Generate a frequency domain signal vector according to at least one digital signal, wherein the at least one digital signal includes movement information of an object and an interference signal caused by an interference in the background, and the frequency domain signal vector includes an energy value and the frequency domain in a time period;

Step 720: Perform spectral subtraction according to the frequency domain signal vector and a frequency domain interference estimation signal vector to generate an amplitude value.

Step 730: Generate a frequency domain detection threshold vector according to the frequency domain interference estimation signal vector and an adjustment parameter.

Step 740: Generate a frequency domain interference estimation signal vector according to the frequency domain signal vector, wherein the frequency domain interference estimation signal vector corresponds to an energy distribution in frequency domain;

Step 750: Optionally provide an error detection control signal to adjust a rate of updating the frequency domain interference estimation signal vector, wherein the error detection control signal is provided according to whether the frequency domain interference estimation signal vector includes Doppler energy of the object movement; and Step 760: Generate a result signal according to the frequency domain signal vector and the frequency domain detection threshold vector, wherein the result signal is related to the movement information of the object.

The detail operation of each step can be found in the above descriptions of FIG. 3 to FIG. 6 and would not be repeated here.

Figure 9:
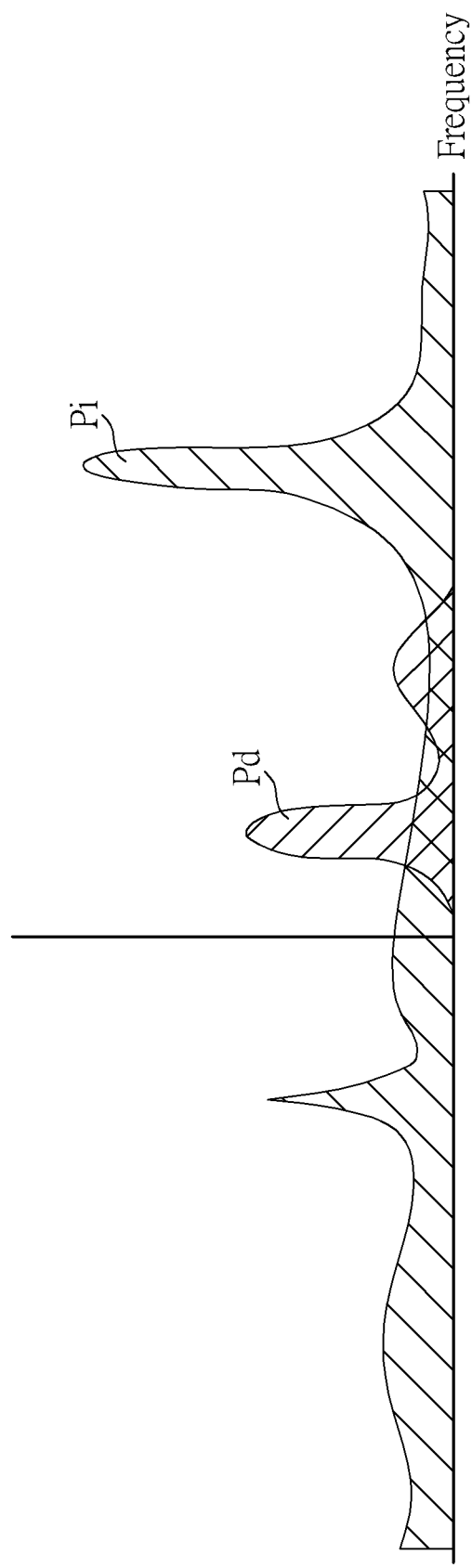
FIG. 9 is a diagram of the Doppler component of the spectrum and the interference baseline component.

FIG. 9 is a diagram of the Doppler component of the spectrum and the interference baseline component. As shown in FIG. 9, the spectral component Pd may be a Doppler component corresponding to the movement information of the object Obj, wherein the frequency is related to the velocity, and the intensity of the component is related to the radar cross-sectional area. The spectral component Pi may be a component corresponding to interference energy baseline in frequency domain. By using the device and method in this invention, the influence of the interference component can be reduced, thereby improving detection accuracy.

By using the device and method provided by the embodiments, the detection result can be dynamically updated according to the received signal, so that tracking control can be achieved. In addition, interference suppression calculations can remove interference energy corresponding to a specific frequency band in the background, thereby improving detection accuracy.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A Doppler signal processing device for detecting an object according to a received wireless signal, the Doppler signal processing device comprising:
    an antenna configured to receive a wireless signal comprising vital sign movement information of the object and an interference signal generated by an interference in a background;
    an analog to digital converter configured to convert the received wireless signal to at least one digital signal;
    a frequency analysis unit, configured to generate a frequency domain signal vector based on the at least one digital signal, wherein the frequency domain signal vector comprises a frequency domain of a time period and a corresponding energy value;
    an interference suppression unit configured to perform a suppression operation according to the frequency domain signal vector and a frequency domain interference estimation signal vector to generate an interference suppressed frequency domain signal vector, wherein energy of the interference in frequency domain is suppressed in the interference suppressed frequency domain signal vector;
    an interference estimation unit configured to generate or update the frequency domain interference estimation signal vector according to the frequency domain signal vector, wherein the frequency domain interference estimation signal vector corresponds to an energy distribution of the interference in the frequency domain;
    a detection unit configured to generate a result signal according to the interference suppressed frequency domain signal vector, wherein the result signal is related to the movement information of the object;
    an error detection unit configured to provide an error detection control signal to the interference estimation unit to adjust a rate of updating the frequency domain interference estimation signal vector, wherein the error detection control signal is provided when the frequency domain interference estimation signal vector includes Doppler energy of an object movement larger than a vital sign movement.

2. The device of claim 1, wherein the interference suppression unit is further configured to generate an amplitude value according to the frequency domain signal vector and the frequency domain interference estimation signal vector, and the error detection unit is further configured to optionally provide then error detection control signal to the interference estimation unit to adjust a rate of updating the frequency domain interference estimation signal vector according to the amplitude value.

3. The device of claim 1, wherein the detection unit comprises:
    a motion detection unit configured to generate a motion detection signal according to the interference suppressed frequency domain signal vector, wherein the motion detection signal corresponds to the larger object movement;
    a switch unit configured to output the interference suppressed frequency domain signal vector when the motion detection signal corresponds to not detecting the large object movement;
    a vital sign detection unit configured to receive the interference suppressed frequency domain signal vector when the motion detection signal corresponds to not detecting the large object movement and to output a vital sign detection signal according to the interference suppressed frequency domain vector, wherein the vital sign detection signal corresponds to a vital sign of the object; and
    an OR gate unit configured to output the result signal according to the motion detection signal and the vital sign detection signal, wherein when the large object movement or the vital sign is detected, the result signal corresponds to detecting the object.

4. The device of claim 1, wherein the detection unit generates the result signal according to a frequency domain detection threshold vector.

5. The device of claim 1, wherein the result signal is used to determine whether the object is detected.

6. The device of claim 2, wherein when the amplitude value exceeds a certain negative value, the error detection unit provides the error detection control signal to the interference estimation unit to adjust the rate of updating the frequency domain interference estimation signal vector, wherein the amplitude value corresponds to an absolute value of one of the frequency domain signal vectors and the difference between the interference estimation signal vector and a second adjustment parameter is subtracted.

7. The device of claim 1, wherein the frequency analysis unit performs a short-time Fourier transform to generate the frequency domain signal vector by using the at least one digital signal, the frequency analysis unit comprising a multi-band filter bank, and the frequency domain signal vector is a multi-band signal vector.

8. The device of claim 1, wherein the interference estimation unit updates the frequency domain interference estimation signal vector according to the result signal.

9. The device of claim 1, wherein the interference estimation unit further comprises:
    an absolute value unit configured to generate an absolute value of one of the frequency domain signal vectors;
    a filtering unit configured to generate a filtered signal vector corresponding to the absolute value according to the absolute value;
    a multiplier configured to generate a product of the frequency domain interference estimation signal vector and a second adjustment parameter; and an adder configured to generate a sum value of the product and one of the filtered signal vector, wherein the sum value is used to update the frequency domain interference estimation signal vector.

10. The device of claim 9, wherein the interference estimation unit further comprises a delay unit configured to delay the sum value by a predetermined time and output to update the frequency domain interference estimation signal vector.

11. A Doppler signal processing device for detecting an object according to a received wireless signal, the Doppler signal processing device comprising:
an antenna configured to receive a wireless signal comprising vital sign movement information of the object and an interference signal generated by an interference in a background;
an analog to digital converter configured to convert the received wireless signal to at least one digital signal;
a frequency analysis unit, configured to generate a frequency domain signal vector based on the at least one digital signal, wherein the frequency domain signal vector comprises a frequency domain of a time period and a corresponding energy value;
an interference subtracting unit configured to perform spectral subtraction according to the frequency domain signal vector and a frequency domain interference estimation signal vector to generate an amplitude value;
a frequency domain detection threshold unit configured to generate a frequency domain detection threshold vector according to the frequency domain interference estimation signal vector and a first adjustment parameter;
a detection unit configured to generate a result signal according to the frequency domain signal vector and the frequency domain detection threshold vector, wherein the result signal is related to the movement information of the object;
an interference estimation unit configured to generate or update the frequency domain interference estimation signal vector according to the frequency domain signal vector, wherein the frequency domain interference estimation signal vector corresponds to an energy distribution in the frequency domain; and
an error detection unit configured to provide an error detection control signal to the interference estimation unit according to the amplitude value to adjust a rate of updating the frequency domain interference estimation signal vector, wherein the error detection control signal is provided when the frequency domain interference estimation signal vector includes Doppler energy of an object movement larger than a vital sign movement.

12. The device of claim 11, wherein the result signal is used to determine whether the object is detected.

13. The device of claim 11, wherein when the amplitude value exceeds a certain negative value, the error detection unit provides the error detection control signal to the interference estimation unit to adjust the rate of updating the frequency domain interference estimation signal vector, wherein the amplitude value corresponds to an absolute value of one of the frequency domain signal vectors and the difference between the interference estimation signal vector and a second adjustment parameter is subtracted.

14. The device of claim 11, wherein the frequency analysis unit performs a short-time Fourier transform to generate the frequency domain signal vector by using the at least one digital signal, the frequency analysis unit comprising a multi-band filter bank, and the frequency domain signal vector is a multi-band signal vector.

15. The device of claim 11, wherein the interference estimation unit updates the frequency domain interference estimation signal vector according to the result signal.

16. The device of claim 11, wherein the interference estimation unit further comprises:
an absolute value unit configured to generate an absolute value of one of the frequency domain signal vectors;
a filtering unit configured to generate a filtered signal vector corresponding to the absolute value according to the absolute value;
a multiplier configured to generate a product of the frequency domain interference estimation signal vector and a second adjustment parameter; and
an adder configured to generate a sum value of the product and one of the filtered signal vector, wherein the sum value is used to update the frequency domain interference estimation signal vector.

17. The device of claim 11, wherein the interference estimation unit further comprises a delay unit configured to delay the sum value by a predetermined time and output to update the frequency domain interference estimation signal vector.

18. A method of signal processing, comprising:
using an antenna to receive a wireless signal comprising vital sign movement information of an object and an interference signal generated by an interference in a background;
using an analog to digital converter to convert the received wireless signal to at least one digital signal;
generating a frequency domain signal vector based on the at least one digital signal, wherein the frequency domain signal vector comprising a frequency domain of a time period and a corresponding energy value;
generating a frequency domain interference estimation signal vector according to the frequency domain signal vector, wherein the frequency domain interference estimation signal vector corresponds to an energy distribution in the frequency domain;
providing an error detection control signal to the interference estimation unit to adjust a rate of updating the frequency domain interference estimation signal vector, wherein the error detection control signal is provided when the frequency domain interference estimation signal vector includes Doppler energy of an object movement larger than a vital sign movement; and
generating a result signal according to the frequency domain signal vector and the frequency domain detection threshold vector wherein the result signal is related to the movement information of the object.

19. The method of claim 18, further comprising:
performing a suppression operation according to the frequency domain signal vector and the frequency domain interference estimation signal vector to generate an interference suppressed frequency domain signal vector, wherein energy interference in frequency domain is suppressed in the interference suppressed frequency domain signal vector.

20. The method of claim 18, further comprising:
performing spectral subtraction based on the frequency domain signal vector and the frequency domain interference estimation signal vector to generate an amplitude value;
generating a frequency domain detection threshold vector according to the frequency domain interference estimation signal vector and an adjustment parameter.

* * * * *